United States Patent [19]
Mukerji et al.

[11] Patent Number: 5,538,952
[45] Date of Patent: * Jul. 23, 1996

[54] INHIBITION OF INFECTION OF MAMMALIAN CELLS BY RESPIRATORY SYNCYTIAL VIRUS

[75] Inventors: Pradip Mukerji, Gahanna; Amanda E.-Y. Seo, both of Gahanna; Steven N. Anderson, Pickerington; Joseph P. Schaller, Columbus, all of Ohio

[73] Assignee: Abbott Laboratories, Abbott Park, Ill.

[*] Notice: The portion of the term of this patent subsequent to May 26, 2014, has been disclaimed.

[21] Appl. No.: 249,555

[22] Filed: May 26, 1994

[51] Int. Cl.$^6$ ............... A61K 38/00; A61K 35/20; C07K 1/00
[52] U.S. Cl. ............... 514/21; 514/12; 530/324; 530/350; 530/360; 530/365; 530/832; 424/535
[58] Field of Search ............... 514/21, 12; 530/324, 530/350, 360, 365, 832; 424/535

[56] References Cited

FOREIGN PATENT DOCUMENTS

| | | |
|---|---|---|
| 0291265 | 7/1988 | European Pat. Off. . |
| WO9106308 | 5/1991 | WIPO . |
| WO9108675 | 6/1991 | WIPO . |
| 93/04171 | 2/1993 | WIPO . |
| WO9304172 | 3/1993 | WIPO . |
| 94/06306 | 5/1994 | WIPO . |

OTHER PUBLICATIONS

Svanborg et al., Adv. Exp. Med. Biol., 310:167–171 (1991).
Tyrell, "Breast Feeding and Virus Infection", The Immunology of Infant Feeding, ed. A. W. Wikinson, Plenum Press, pp. 55–62 (1981).
Anderson et al., "Microneutralization Test for Respiratory Syncitial Virus Based on an Enzyme Immunoassay", Journal of Clinical Microbiology, 22:1050–1052 (1985).
Laegrid et al., "Neutralizing Activity in Human Milk Fractions Against Respiratory Syncytial Virus", Acta Pediatrica Scandanavica, 75:696–701 (1986).
Okamoto et al., "Antiviral Factors in Human Milk: Implications in Respiratory Syncitial Virus Incfection", Acta Paediatrica Scandinavica Supplement, 351:137–143 (1989).
Lönnerdal et al., "Cloning and Sequencing of a cDNA Encoding Human B–Casein", Federation of European Biochemical Society Letters, 269(1):153–156 (1990).
Hannson et al., "Expression of Human Milk B–Casein in *Escheria coli*: Comparison of Recombinant Protein with Native Isoforms", Protein Expression and Purification, 4:373–381 (1993).
Anianson et al., "Anti–adhesive Activity of Human Casein Against *Strepococcus pneumoniae* and *Haemophilus influenzae*", Microbial Pathogenesis, 8:315–323 (1990).
"Respitory Syncitial Virus or Influenza in Adults", Pediatric Notes, 18(4):1 (1994).
Caegneid et al, Acta Pediatrica Scandinavica, volume 75, pp. 696–701, 1986.

*Primary Examiner*—Christina Y. Chan
*Assistant Examiner*—Abdel A. Mohamed
*Attorney, Agent, or Firm*—Lonnie R. Drayer

[57] ABSTRACT

The infection of mammalian cells by RSV may be inhibited by native human β-casein, a recombinant form of human β-casein, and hydrolysates of both. The human β-casein or hydrolysate may be contained in a liquid enteral nutritional product such as an infant formula. The enteral nutritional product may be used, for example, in the prevention and treatment of respiratory tract infection in infants. The human β-casein or hydrolysate may also be administered as a throat spray or nasally using drops or a spray.

4 Claims, No Drawings

INHIBITION OF INFECTION OF MAMMALIAN CELLS BY RESPIRATORY SYNCYTIAL VIRUS

The present invention relates generally to inhibiting the infection of mammalian cells by Respiratory Syncytial Virus, and more specifically to the use of native or recombinant human β-casein and hydrolysates thereof for inhibiting the infection of mammalian cells by Respiratory Syncytial Virus.

Respiratory Syncytial Virus (RSV) is the single most frequent cause of acute respiratory tract infection in infants and children. Infants less than six months of age are most frequently and seriously affected. In most immunologically normal subjects, infection with RSV is limited to the respiratory mucosa, and is associated with the development of bronchiolitis, pneumonia and reactive airway disease. RSV infection in immunocompromised subjects has until recently been associated with increased mortality in infants and increased morbidity in other age groups. It has recently been reported in *PEDIATRIC NOTES*, Vol. 18, No. 4, Jan. 27, 1994, that periods of high incidence of acute respiratory disease and numbers of deaths in elderly people were followed within 2–3 weeks by reports of high numbers of RSV or influenza virus isolates. The analyses indicate that RSV is as important as influenza viruses in causing morbidity and deaths among the elderly.

It has been reported that some respiratory disease may be prevented by breast feeding, and that *"bronchiolitis of infants* due to respiratory syncytial virus is less frequent in breast fed than in artificially fed infants". While human breast milk can contain antibodies to RSV, it has been found that milk also has antiviral activity that is not due to antibodies. It has been theorized that this effect "may be produced by certain polysaccharides which are found on a number of different molecular constituents of milk." Tyrrell, "BREAST FEEDING AND VIRUS INFECTIONS", *THE IMMUNOLOGY OF INFANT FEEDING*, edited by A. W. Wilkinson, Plenum Press, New York, N.Y. pages 55–62 (1981).

Okamato, et al., "Antiviral Factors in Human Milk: Implications in Respiratory Syncytial Virus Infection", *ACTA PAEDIATRICA SCANDANAVICA SUPPLEMENT*, 351:137–143 (1989) disclose that while the mechanisms of protective immunity to RSV had not been clearly defined, immunity acquired transplacentally or via breast feeding has been suggested to reduce the risk of lower respiratory tract disease. However, this publication focuses upon the role of antibodies transmitted in breast milk or the possible role of breast milk in modulating an infant's RSV immune response.

Laegreid et al., "Neutralizing Activity in Human Milk-Fractions against Respiratory Syncytial Virus", *ACTA PAEDIATRICA SCANDANAVICA*, 75:696–701 (1986) reports a study which confirms that human milk may contain RSV-neutralizing activity of a non-immunoglobulin nature as well as RSV-specific antibody. However, the identity and mechanism of the non-immunoglobulin anti-RSV component of human milk is not identified. It is important though to note that Laegreid et al. disclose that RSV-neutralizing components from breast milk may reach an infant's respiratory tract directly as a result of regurgitation and inhalation of milk during and after feeding. The mucosa of the respiratory tract may gain direct protection in this way.

WO 91/06308 filed by Andersson et al. for "ANTIBACTERIAL COMPOSITION", and a published article by the same authors (Aniansson et al., "Anti-adhesive activity of human casein against Streptococcus pneumonia and Haemophilus influenzae", *MICROBIAL PATHOGENESIS*, 8:315–323 (1990) disclose the use of a milk fraction having a molecular weight of at least 5,000 daltons for "therapeutic prophylactic, and/or diagnostic use in infections caused by *S. pneumonae* and/or *H. influenzae*", but it is suggested in these publications that the beneficial effect is provided by kappa-casein. However, the present invention relates to the use of native or recombinant human β-casein and hydrolysates of both to inhibit RSV infections.

WO93/04172 relates to a DNA sequence encoding human β-casein, but does not disclose the capacity of either native or recombinant human β-casein to inhibit the attachment of RSV to human cells.

WO91/08675 discloses an infant formula which contains recombinant forms of both human alpha-lactalbumin and human β-casein. However, this publication discloses only that these human milk proteins will "give a simulated human mother's milk formula that does not exhibit the allergenic properties associated with formulas based on cow or other foreign protein." (page 3, lines 20–22). The use of human β-casein to inhibit the attachment of RSV to human cells is not taught or suggested in said publication.

The two assays (a HEp-2 cell assay and a LLC-MK2 cell assay) which were used for determining the bioactivity of β-casein are described below. These assays have not been published heretofore, although the HEp-2 cell assay was based upon established methodology.

MATERIALS USED IN BOTH ASSAYS

Native Human β-Casein

β-casein isolated from human milk was purchased from Symbicom AB, P.O. Box 1451, S-901 24 Umea, Sweden.

Recombinant Human β-Casein

Applicants obtained β-casein cDNA and the expression system from Symbicom AB, P.O. Box 1451, S-901 24 Umea, Sweden. The human β-casein cDNA used had been previously cloned and sequenced by Lonnerdal et al., Cloning and sequencing of a cDNA encoding human milk β-casein. (SEQ.ID NO: 1:) *Federation of European Biochemical Societies Letters* 269, 153–156 (1990). The recombinant human β-casein was obtained from *E. coli* and purified according to the method of Hansson et al.,Expression of Human Milk β-Casein in *Escherichia coli*: Comparison of Recombinant Protein with Native Isoforms. *Protein Expression and Purification* 4, 373–381 (1993). To express human β-casein in *E. coli*, β-casein cDNA was cloned under control of a T7 promoter in two different expression vectors. One vector, pS26, was designed for intracellular expression. The other vector, pS28, has a signal sequence for extracellular expression. The procedure followed was substantially that described by Hansson et al.

Human β-casein cDNA was isolated by Hansson et al. as a 1.1-kb EcoRI fragment from a human lambda gt mammary gland library, and was subcloned into pUC19, which was designated pS21. The cDNA was modified by introduction of synthetic oligonucleotides in the 5' and 3' termini. To introduce a suitable cloning site in the 5' end, NdeI, a translational start, was inserted in front of the sequence encoding mature human β-casein. To adapt the initial part of the translated sequence to *E. coli* codon usage, six synthetic oligonucleotides were constructed and ligated. Also, PstI and EcoRI sites were inserted in front of the NdeI site. The sequence of the synthetic fragment was 5'-CTGCAGAAT-TCATATGCGT GAAACCATCGAATCCCTGAGCTC-GAGCGAAGAATCGATCACCGAATA-CAAAAAAGTTGAAAAAGTTAAACACGAGGACCA GGATCC-3'. (SEQ ID NO: 2:) The protein encoding sequence is underlined. The synthetic fragment was cloned into PstI/BamHI-digested pUC19 resulting in plasmid pS24. To insert the rest of the β-casein encoding sequence, a 303-bp AccI/BglII fragment was isolated and cloned into a pUC18 derivative and designated plasmid pS22. Four synthetic oligonucleotides containing the sequence encoding the carboxy-terminal end and translation stop followed by BamHI and EcoRI sites were constructed resulting in the sequence 5'AGATCTACCCTGTGA CTCAGCCACTTGC-CCCAGTTCATAACCCCATTAGT-GTCTAATAAGGATCCGAATTC-3', (SEQ ID NO: 3:) where the protein encoding sequence is underlined. The synthetic fragment was cloned into BglII/EcoRI digested pS22, resulting in plasmid pS23. To obtain the recombinant modified β-casein encoding fragment, three fragments were ligated: an 89-bp PstI/AvaII fragment from pS24; a 197-bp AvaII/AccI fragment from pS21; and PstI/AccI digested pS23. The resulting plasmid pS25 was digested with NdeI/BamHI and a 641-bp fragment was isolated and cloned into the vector pET-3a. The resulting expression vector was designated pS26.

In order to construct a vector mediating extracellular expression, the *E. coli* signal sequence of the enterotoxin STII gene was introduced in front of the β-casein encoding sequence. A modified STII sequence with NcoI- and NdeI-compatible ends and an internal ClaI site was obtained by using a synthetic oligonucleotide, 5'-CATGAAAAA-GAATATCGCATTTCTTCTTGCATCGATGTTCGTTT TTTCTATTGCTACAAATGCATATG-3' (SEQ ID NO: 4:). To insert the signal sequence in front of the β-casein encoding sequence, pS25 was digested with AvaI/EcoRI and a 619-bp fragment was isolated. This fragment was ligated with a synthetic oligonucleotide fragment, 5'CATATG-CACGTGAAACCATCGAATCCCTGAGCTCGAG-3' (SEQ ID NO: 5:), and NdeI/EcoRI-digested pUC19. The resulting plasmid was designated pS27. The final expression vector,pS28, was constructed by ligating three fragments: a 700-bp NdeI/HindIII β-casein fragment isolated from pS27, the STII signal sequence, and a NcoI/HindIII-digested pACAT7 vector.

The expression vectors pS26 and pS28 were used to transform *E. coli* strains BL21(DE3), BL21(DE3)pLysS, and BL21(DE3)pLysE. The bacteria were grown in Luria Broth medium containing 50 µg/ml carbenicillin, and when B121(DE3)pLysS and BL21(DE3)pLysE were used the medium was supplemented with 25 µg/ml chloramphenicol.

For induction of expression the cultures were grown to a density yielding an optical density (OD) of 0.6 at a wavelength of 600 nanometers ($OD_{600}$), then 0.4 mM IPTG was added to induce the T7 system. The cells were harvested about 90 minutes after induction.

Recombinant β-casein was isolated using standard procedures. The inducible T7-based expression system resulted in high-level expression of recombinant β-casein. Bacteria were harvested and the cells pelleted by centrifugation. The supernatant contained the periplasmic proteins and the pellet the cytoplasmic fraction. The recombinant proteins obtained were compared with native β-casein, which had been purified by standard methods including either ion-exchange chromatography followed by reversed-phase HPLC or gel filtration. Recombinant and native β-casein were compared by standard biochemical techniques comprising SDS-PAGE, Western blotting, amino acid analysis, peptide mapping, phosphate analysis, and mass spectrometry. Recombinant β-casein expressed in *E. coli* was found to comigrate with full-length, nonphosphorylated native human β-casein, which is one of seven native isoforms.

Recombinant human β-casein has also been expressed in *S. cerevisiae* using the pYES 2.0 vector (Invitrogen Corp., San Diego, Calif.), but the expression level was approximately 10% of that obtained in *E. coli*. However, Hansson et al. found that *S. cerevisiae* appeared to express phosphorylated human milk β-casein.

β-Casein Hydrolysates

The human β-casein (both native and recombinant) was digested using the specific endoproteinase GLU-C (Sigma, sequencing grade) which catalyzes the hydrolysis of peptide bonds at the C-terminal of glutamic acid residue. After monitoring the digest using high pressure liquid chromatography, an enzyme to protein ratio of 1:100 (weight/weight) was chosen for a 30 hour digestion at 37° C. in 0.1M $NH_4HCO_3$, pH 7.8. These digests were dried and resuspended in appropriate buffers prior to use in the assays discussed above.

INHIBITION OF HUMAN RSV INFECTION OF HEp-2 CELLS

The Long strain of RSV was grown in HEp-2 cells under Eagle minimal essential medium (MEM) with 2% fetal bovine serum (FBS). The virus was harvested at a cytopathic effect (CPE) of 3 to 4+, sonicated for 10 seconds at 50% power with a Microson ultrasonic bell disrupter (Heat Systems—Ultrasonics, Inc., Farmingdale, N.Y.), divided into portions and stored at −70° C. The same preparation of virus was used for a series of tests, but a fresh sample was used for each test run.

The neutralization tests were performed in 96-well, flat-bottomed, tissue culture, microtiter plates (catalog no. 3596; Costar, Cambridge, Mass.). Serum or a monoclonal antibody (MAb) in the form of ascites fluid, which had been heat inactivated at 56° C. for 30 min., was added to duplicate wells and serial fourfold dilutions were performed in the microtiter plates. All dilutions were in MEM-2% FBS, and the final volume was 75 µl per well. Approximately 60 50% tissue culture infective doses of virus in 25 µl of MEM-2% FBS then were added to each well, and the mixture was incubated for 2 h at 4° C.

Approximately 15,000 HEp-2 cells in 100 µl of MEM-5% FBS were added to each well, and the plates were wrapped in cellophane and incubated at 35.5° C. in a humidified $CO_2$ incubator for 3 days. The plates were fixed by aspirating the contents of the wells, washing three times with phosphate-buffered saline (PBS) at pH 7.2 with 0.5% Tween 20, adding 75 µl of an 80% (vol/vol) solution of acetone-PBS, and incubating for 15 min at 4° C. After the incubation period, the contents were aspirated, and the plates were air dried.

The Enzyme Linked Immuno Sorbent Assay (ELISA) was performed on the same day as the fixation, or the plates were stored overnight at 4° C. and the ELISA was performed on the next day. For the ELISA, the wells were precoated with 200 µl of PBS with 0.5% gelatin for 30 min at 35° C., the contents were aspirated, the wells were washed with PBS (pH 7.2)-0.5% Tween 20 and 75 µl of bovine anti-RSV serum (BaRSV) Burroughs Wellcome Co., Research Triangle Park, N.C.) diluted in PBS 0.5% gelatin plus 0.5% Tween 20 and 2% normal goat serum was added and incubated for 1 hour at 35.5° C. The contents were aspirated, the wells were washed, and 75 µl of peroxidase-conjugated, goat anti-bovine immunoglobulin G (IgG) (Kirkegaard and Perry Laboratories, Inc., Gaithersburg, Md.) diluted in PBS-0.5% gelatin-0.5% Tween 20–2% normal goat serum was added and incubated for 1 hour at 35.0° C. The contents of the wells were aspirated again, the wells were washed, and 125 µl of substrate (0.4 mg of o-phenylenediamine dihydrochloride per ml 0.015% $H_2O_2$) in 0.15M citrate phosphate buffer (pH 5.5) was added and incubated at room temperature for 40 to 45 min. The reaction was stopped with 3.5M HCl, and the $A_{490}$ was read with a microplate reader. Each dilution of antibody was run in duplicate, and each plate included control wells with uninfected cells, a back titration, i.e. titration of the virus inoculum in MEM-2% FBS, and a titration of a preimmune or nonneutralizing antibody. An absorbance reading of greater than or equal to 3 standard deviations above the mean of 15 control wells was considered to be evidence of virus replication. The dilutions of BaRSV (1:1,000) and goat anti-bovine IgG (1:5,000) used through the study initially was determined by checkerboard titrations.

This assay was based upon the disclosure of Anderson et al., "Microneutralization Test for Respiratory Syncytial Virus Based on an Enzyme Immunoassay", *JOURNAL OF CLINICAL MICROBIOLOGY*, December 1985, pages 1050–1052.

RESULTS FROM HEp-2 CELL ASSAY

The human and bovine β-casein solutions were prepared first in 20 mM ethanolamine, 6M urea, pH 9.5 and then washed twice in PBS by ultrafiltration using Centricon membrane filters (Amicon, Mass.) with a cut-off of 3,000 daltons. After resuspending in appropriate buffer for the HEp-2 cell assay described above, these samples were tested in the assay. Experiments with different designated numbers were performed in different days. As shown in Table 1, human β-casein caused an inhibition of infection/virus replication of 50% or more at concentrations of 0.4 mg/ml or greater. It should be noted than when referring to Table 1, a higher percent inhibition indicates a higher level of bioactivity of the "AGENT", and a lower percent inhibition indicates a lower level of activity of the "AGENT". Bovine β-casein was not significantly active even at 1.6 mg/ml. These results indicated that β-casein from human milk has different bioactivity compared to the bovine milk β-casein.

TABLE 1

INHIBITION OF HUMAN RSV
INFECTION OF HEp-2 CELLS

| AGENT USED | CONC. (mg/ml) | PERCENT INHIBITION |
|---|---|---|
| β-Casein Isolated from Human Milk | 1.6 | >90 |
| | 0.8 | >90 |
| | 0.4 | >90 |
| Bovine β-casein | 1.6 | 0 |
| | 0.8 | 0 |
| | 0.4 | 0 |

Data shown are average of three replicates.

INHIBITION OF HUMAN RSV INFECTION OF LLC-MK2 CELLS

The RSV inhibition assay quantitatively determines the ability of a test reagent (antibody or other bioactive compound) to inhibit the infection of monkey kidney cells (LLC-MK2) (ATCC CCL 7) in microtiter plates. Infected cells were identified using an immunoperoxidase method. The method is described briefly below.

LLC-MK2 cells were seeded into fibronectin treated Costar microtiter plates ($5.0 \times 10^3$ cells per well) and incubated for 3–4 days prior to use in the infectivity reduction assay. On the day of assay, the Long strain of RSV was diluted in MEM to 10–20,000 infected cell units (ICU/mL), and added to an equal volume (200 μL) of serially diluted sample preparations at suitable concentration (ex. 0.5, 1.0, and 2.0 mg casein/mL). Mixtures of diluted test samples and virus were then incubated for 2 hours at 4° C. prior to adding to LLC-MK2 cells. Prior to addition of the diluted sample-virus mixtures to microtiter plates, culture medium was removed and the monolayers rinsed one time with MEM. All diluted sample-virus mixtures were tested in triplicate wells. The diluted sample-virus mixtures were allowed to absorb to LLC-MK2 monolayers for 2 hours at 37° C. in a humidified $CO_2$ incubator. Following incubation, 150 μl of MEM was added to all wells and the plates incubated at 37° C. for 16 hours in the $CO_2$ incubator. After overnight incubation, the culture medium was removed and the monolayers fixed with cold ethanol. After fixing, microtiter plates were rinsed once with 200 μl Dulbecco's PBS per well, and bovine anti-RSV antibody (200 μl) was added to all wells. Following a 30 minute incubation at room temperature and three rinses with PBS/0.5% chick albumen (PBS/CEA), peroxidase labeled rabbit anti-bovine IgG was added to all wells and incubated at room temperature for 30 minutes. Microtiter plates were then rinsed 3 times with PBS/CEA and diaminobenzidine substrate added and incubated for 20 minutes. Plates were then rinsed as above with PBS/CEA, and the number of stained RSV-infected cells per well determined using an inverted microscope.

RESULTS FROM LLC-MK2 CELL ASSAY

The proteins described in Table 1 were also tested in this assay for activity Once again, native human milk β-casein was found to be active at concentrations of 1 mg/ml or greater while bovine β-casein was not significantly active. The GLU-C hydrolysates of both native and recombinant human β-casein were active at concentrations of 0.75 mg/ml and higher. Hence these results indicated that the recombinant human β-casein, native human β-casein and their hydrolysates inhibit RSV infection of both HEp-2 mammalian cells and LLC-MK2 mammalian cells.

TABLE 2

INHIBITION OF HUMAN RSV
INFECTION OF LLC-MK2 CELLS

| AGENT USED | CONC. (mg/ml) | PERCENT INHIBITION |
|---|---|---|
| β-Casein Isolated from Human Milk | 1.5 | 87 |
| | 1 | 69 |
| | 0.75 | 33 |
| | 0.38 | 20 |
| Bovine β-casein | 1 | 21 |
| | 0.5 | 23 |
| | 0.25 | 6 |
| Hydrolysate of β-casein Isolated from Human Milk | 1.5 | 99 |
| | 0.75 | 77 |
| | 0.38 | 60 |
| Hydrolysate of Recombinant Human β-Casein | 1.5 | 84 |
| | 0.75 | 42 |
| | 0.38 | 25 |
| GLU-C Enzyme Control | .025 | 64 |
| | .0125 | 27 |
| | .0068 | 19 |

Data shown are average of four replicates.

It has been concluded from the foregoing experiments that β-casein isolated from human milk, a recombinant form of the β-casein contained in human milk, and hydrolysates of both, inhibits the infection of mammalian cells by RSV.

Furthermore, inasmuch as RSV has been identified in the literature as being associated with respiratory tract infection, it has been concluded that the above identified forms of human β-casein may be employed in the prevention and treatment of respiratory tract infection in humans, especially in human infants. In view of the therapeutic effect of enterally ingested human milk containing human β-casein upon respiratory tract infection, it is concluded that the above identified forms of human β-casein have a therapeutic benefit when enterally (orally) ingested.

The therapeutic effects described in the preceding paragraph may be provided by an enteral liquid nutritional product, such as infant formula, comprising one or more proteins not contained in human milk in combination with a therapeutically effective amount of at least one of the forms of human β-casein described in the preceding paragraph. It is further concluded that the infection of mammalian cells by RSV may be inhibited by administering via a nasal passageway, or as a throat spray, a formulation containing a therapeutically effective amount of at least one of the forms of human β-casein identified in the preceding paragraph. Such a nasally administered formulation may be in the form of either drops or a spray.

The enteral nutritional, throat spray and nasal products and methods are believed to be effective in inhibiting the infection of mammalian cells by RSV because the interaction of the human β-casein and RSV is believed to occur via direct contact rather than following digestion and absorption of the β-casein.

It is believed that the above identified forms of human β-casein may be incorporated into any standard or specialized enteral liquid nutritional product containing at least one protein not found in human milk, such as bovine milk based or soy based infant formulas, and other beverages consumed by young children. In a preferred embodiment no proteins or hydrolysates thereof found in human milk, other than β-casein, are contained in the liquid enteral nutritional product. Such a product has utility in the treatment and prevention of respiratory tract infection in human infants.

While preferred embodiments of the invention have been disclosed, it will be apparent to those skilled in the art that various changes and modifications may be made therein without deviating from the spirit or scope of this invention.

---

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
    ( A ) LENGTH:1065 base pairs
    ( B ) TYPE:Nucleic acid
    ( C ) STRANDEDNESS: Single
    ( D ) TOPOLOGY: Unknown ( i i ) MOLECULE TYPE: Cloned cDNA representing the product of a human
    genomic DNA segment.
    ( A ) DESCRIPTION: Human milk acta- casein ( i i i ) HYPOTHETICAL:

( i v ) ANTI-SENSE:
  ( v ) FRAGMENT TYPE:

( v i ) ORIGINAL SOURCE: Human
    ( A ) ORGANISM: Homo sapiens
    ( B ) STRAIN:
    ( C ) INDIVIDUAL ISOLATE:
    ( D ) DEVELOPMENTAL STAGE: Adult
    ( E ) HAPLOTYPE:
    ( F ) TISSUE TYPE: Mammary gland
    ( G ) CELL TYPE:
    ( H ) CELL LINE:
    ( I ) ORGANELLE:

( v i i ) IMMEDIATE SOURCE: Human Mammary Gland
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD: DNA sequencing and restriction
      analysis
    ( D ) OTHER INFORMATION: The encoded product of nucleotide SEQ ID NO: 1: is the human milk protein, B-casein.

(x) PUBLICATION INFORMATION:
    (A) AUTHORS: B. Lonnerdal et al
    (B) TITLE: Cloning and sequencing of a cDNA encoding human milk beta- casein.
    (C) JOURNAL:Federation European Biochemical Society Letters
    (D) VOLUME:269
    (E) ISSUE:
    (F) PAGES:153 - 156
    (G) DATE:1990
    (H) DOCUMENT NUMBER:
        (I) FILING DATE:
    (J) PUBLICATION DATE:
    (K) RELEVANT RESIDUES IN SEQ ID NO:

(xi) SEQUENCE DESCRIPTION: SEQ ID NO: 1:

```
CGG ATG AAG GTC CTC ATC CTC GCC TGC CTG GTG GCT CTT GCT CTT    45
GCA AGG GAG ACC ATA GAA AGC CTT TCA AGC AGT GAG GAA TCT ATT    90
ACA GAA TAC AAG AAA GTT GAG AAG GTT AAA CAT GAG GAC CAG CAG   135
CAA GGA GAG GAT CAC CAG GAT AAA ATC TAC CCC TCT TTC CAG       180
CCA CAG CCT CTG ATC TAT CCA TTC GTT GAA CCT ATC CCC TAT GGT   225
TTT CTT CCA CAA AAC ATT CTG CCT CTT GCT CAG CCT GCT GTG GTG   270
CTG CCT GTC CCT CAG CCT GAA ATA ATG GAA GTC CCT AAA GCT AAA   315
GAC ACT GTC TAC ACT AAG GGC AGA GTG ATG CCT GTC CTT AAA TCT   360
CCA ACG ATA CCC TTT TTT GAC CCT CAA ATC CCA AAA CTC ACT GAT   405
CTT GAA AAT CTG CAT CTT CCT CTG CCT CTG CTC CAG CCC TTG ATG   450
CAG CAG GTC CCT CAG CCT ATT CCT CAG ACT CTT GCA CTT CCC CCT   495
CAG CCC CTG TGG TCT GTT CCT CAG CCC AAA GTC CTG CCT ATC CCC   540
CAG CAA GTG GTG CCC TAC CCT CAG AGA GCT GTG CCT GTT CAA GCC   585
CTT CTG CTC AAC CAA GAA CTT CTA CTT AAC CCC ACC CAC CAG ATC   630
TAC CCT GTG ACT CAG CCA CTT GCC CCA GTT CAT AAC CCC ATT AGT   675
GTC TAA GAA GAT TTC AAA GTT AAT TTT CCC TCC TTA TTT TTG AAT   720
TGA CTG AGA CTG GAA ATA TGA TGC CTT TTC CGT CTT TGT ATC ACG   765
TTA CCC CAA ATT AAG TAT GTT TGA ATG AGT TTA TAT GGA AAA AAT   810
GAA CTT TGT CCC TTT ATT TAT TTT ATA TAT TAT GTC ATT CAT TTA   855
ATT TGA AAT TTG ACT CAT GAA CTA TTT ACA TTT TCC AAA TCT TAA   900
TTC AAC TAG TAC CAC AGA AGT TCA ATA CTC ATT TGG AAA TGC TAC   945
AAA CAT ATC AAA CAT ATG TAT ACA AAT TGT TTC TGG AAT TGT GCT   990
TAT TTT TAT TTC TTT AAG AAT CTA TTT CCT TTC CAG TCA TTT CAA 1035
TAA ATT ATT CTT AAG CAT AAA AAA AAA AAA                     1065
```

(2) INFORMATION FOR SEQ ID NO: 2:

(i) SEQUENCE CHARACTERISTICS:
        (A) LENGTH:105 base pairs
        (B) TYPE:Nucleic acid
        (C) STRANDEDNESS: Single
        (D) TOPOLOGY: Unknown (ii) MOLECULE TYPE: Synthetic oligonucleotide.
        (A) DESCRIPTION:

(iii) HYPOTHETICAL:

(iv) ANTI-SENSE:
        (v) FRAGMENT TYPE:

(vi) ORIGINAL SOURCE: Synthetic Oligonucleotide Sequence
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
            (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:

(B) LOCATION:
        (C) IDENTIFICATION METHOD: DNA sequencing and restriction
            analysis
        (D) OTHER INFORMATION: The synthetic oligonucleotide assures
            adaptation of translation sequence to E. coli codon
            usuage.

(x) PUBLICATION INFORMATION:
        (A) AUTHORS: L. Hansson et al
        (B) TITLE: Expression of Human Milk a-casein in Escherichia
            coli: Comparison of Recombinant Protein with Native
            Isoforms.
        (C) JOURNAL:Protein Expression and Purification
        (D) VOLUME:4
        (E) ISSUE:
        (F) PAGES:373 - 381
        (G) DATE:1993
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 2:
        CTG CAG AAT TCA TAT GCG TGA AAC CAT CGA ATC CCT GAG CTC GAG    45
        CGA AGA ATC GAT CAC CGA ATA CAA AAA AGT TGA AAA AGT TAA ACA    90
        CGA GGA CCA GGA TCC                                           105

(2) INFORMATION FOR SEQ ID NO: 3:

(i) SEQUENCE CHARACTERISTICS:
        (A) LENGTH:71 base pairs
        (B) TYPE:Nucleic acid
        (C) STRANDEDNESS: Single
        (D) TOPOLOGY: Unknown (ii) MOLECULE TYPE: Synthetic oligonucleotide.
        (A) DESCRIPTION:

(iii) HYPOTHETICAL:

(iv) ANTI-SENSE:
                (v) FRAGMENT TYPE:

(vi) ORIGINAL SOURCE: Synthetic Oligonucleotide Sequence
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
                (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD: DNA sequencing and restriction
            analysis
        (D) OTHER INFORMATION: The synthetic oligonucleotide encodes
            the carboxy- terminal end and translation stop.

(x) PUBLICATION INFORMATION:
        (A) AUTHORS: L. Hansson et al
        (B) TITLE: Expression of Human Milk a-casein in Escherichia
            coli: Comparison of Recombinant Protein with Native
            Isoforms.
        (C) JOURNAL:Protein Expression and Purification
        (D) VOLUME:4
        (E) ISSUE:
        (F) PAGES:373 - 381

(G) DATE:1993
(H) DOCUMENT NUMBER:
    (I) FILING DATE:
(J) PUBLICATION DATE:
(K) RELEVANT RESIDUES IN SEQ ID NO:

(xi) SEQUENCE DESCRIPTION: SEQ ID NO: 3:

```
AGA TCT ACC CTG TGA CTC AGC CAC TTG CCC CAG TTC ATA ACC CCA    45
TTA GTG TCT AAT AAG GAT CCG AAT TC                              71
```

(2) INFORMATION FOR SEQ ID NO: 4:

(i) SEQUENCE CHARACTERISTICS:
      (A) LENGTH:68 base pairs
      (B) TYPE:Nucleic acid
      (C) STRANDEDNESS: Single
      (D) TOPOLOGY: Unknown (ii) MOLECULE TYPE: Synthetic oligonucleotide.
      (A) DESCRIPTION:

(iii) HYPOTHETICAL:

(iv) ANTI-SENSE:
  (v) FRAGMENT TYPE:

(vi) ORIGINAL SOURCE: Synthetic Oligonucleotide Sequence
      (A) ORGANISM:
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
          (I) ORGANELLE:

(vii) IMMEDIATE SOURCE:
      (A) LIBRARY:
      (B) CLONE:

(viii) POSITION IN GENOME:
      (A) CHROMOSOME/SEGMENT:
      (B) MAP POSITION:
      (C) UNITS:

(ix) FEATURE:
      (A) NAME/KEY:
      (B) LOCATION:
      (C) IDENTIFICATION METHOD: DNA sequencing and restriction
          analysis
      (D) OTHER INFORMATION: Modified enterotoxin STII signal sequen (x) PUBLICATION INFORMATION:
      (A) AUTHORS: L. Hansson et al
      (B) TITLE: Expression of Human Milk a-casein in Escherichia
          coli: Comparison of Recombinant Protein with Native
          Isoforms.
      (C) JOURNAL:Protein Expression and Purification
      (D) VOLUME:4
      (E) ISSUE:
      (F) PAGES:373 - 381
      (G) DATE:1993
      (H) DOCUMENT NUMBER:
          (I) FILING DATE:
      (J) PUBLICATION DATE:
      (K) RELEVANT RESIDUES IN SEQ ID NO:

(xi) SEQUENCE DESCRIPTION: SEQ ID NO: 4:

```
CAT GAA AAA GAA TAT CGC ATT TCT TCT TGC ATC GAT GTT CGT TTT    45
TTC TAT TGC TAC AAA TGC ATA TG                                  68
```

(2) INFORMATION FOR SEQ ID NO: 5:

(i) SEQUENCE CHARACTERISTICS:
      (A) LENGTH:37 base pairs
      (B) TYPE:Nucleic acid
      (C) STRANDEDNESS: Single
      (D) TOPOLOGY: Unknown ( i i ) MOLECULE TYPE: Synthetic oligonucleotide.
                ( A ) DESCRIPTION:

( i i i ) HYPOTHETICAL:

( i v ) ANTI-SENSE:
                    ( v ) FRAGMENT TYPE:

( v i ) ORIGINAL SOURCE: Synthetic Oligonucleotide Sequence
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                        ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD: DNA sequencing and restriction
                    analysis
                ( D ) OTHER INFORMATION:

( x ) PUBLICATION INFORMATION:
                ( A ) AUTHORS: L. Hansson et al
                ( B ) TITLE: Expression of Human Milk a-casein in Escherichia
                    coli: Comparison of Recombinant Protein with Native
                    Isoforms.
                ( C ) JOURNAL:Protein Expression and Purification
                ( D ) VOLUME:4
                ( E ) ISSUE:
                ( F ) PAGES:373 - 381
                ( G ) DATE:1993
                ( H ) DOCUMENT NUMBER:
                        ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO: 5:
            CAT  ATG  CAC  GTG  AAA  CCA  TCG  AAT  CCC  TGA  GCT  CGA  G        3 7

We claim:

1. A method of inhibiting the infection of mammalian cells by respiratory syncytial virus by enterally ingesting a liquid nutritional product comprising at least one protein not contained in human milk but selected from the group consisting of bovine milk protein and vegetable protein in combination with a therapeutically effective amount of at least one material selected from the group consisting of β-casein isolated from human milk, a recombinant form of the β-casein contained in human milk and hydrolysates of both.

2. A method of inhibiting the infection of mammalian cells by respiratory syncytial virus in a human infant by enterally feeding to said human infant an infant formula comprising at least one protein not contained in human milk but selected from the group consisting of bovine milk protein and vegetable protein in combination with a therapeutically effective amount of at least one material selected from the group consisting of β-casein isolated from human milk, a recombinant form of the β-casein isolated from human milk and hydrolysates of both.

3. A method of inhibiting the infection of mammalian cells by respiratory syncytial virus by administering via a nasal passageway a formulation containing a therapeutically effective amount of at least one material selected from the group consisting of β-casein isolated from human milk, a recombinant form of the β-casein contained in human milk and hydrolysates of both.

4. A method of inhibiting the infection of mammalian cells by respiratory syncytial virus by administering a throat spray formulation containing a therapeutically effective amount of at least one material selected from the group consisting of β-casein isolated from human milk, a recombinant form of the β-casein contained in human milk and hydrolysates of both.

* * * * *